(12) United States Patent
Li et al.

(10) Patent No.: US 10,709,454 B2
(45) Date of Patent: Jul. 14, 2020

(54) LEFT ATRIAL APPENDAGE OCCLUDER

(71) Applicant: Lifetech Scientific (Shenzhen) Co., Ltd., Shenzhen (CN)

(72) Inventors: Anning Li, Shenzhen (CN); Yixian Lin, Shenzhen (CN)

(73) Assignee: LIFETECH SCIENTIFIC (SHENZHEN) CO., LTD., Shenzhen (CN)

( * ) Notice: Subject to any disclaimer, the term of this patent is extended or adjusted under 35 U.S.C. 154(b) by 287 days.

(21) Appl. No.: 15/035,824

(22) PCT Filed: Nov. 7, 2014

(86) PCT No.: PCT/CN2014/090605
§ 371 (c)(1),
(2) Date: May 11, 2016

(87) PCT Pub. No.: WO2015/070733
PCT Pub. Date: May 21, 2015

(65) Prior Publication Data
US 2016/0287261 A1    Oct. 6, 2016

(30) Foreign Application Priority Data
Nov. 14, 2013 (CN) .......................... 2013 1 0567987

(51) Int. Cl.
*A61B 17/12* (2006.01)

(52) U.S. Cl.
CPC .. *A61B 17/12172* (2013.01); *A61B 17/12031* (2013.01); *A61B 17/12122* (2013.01); *A61B 17/12177* (2013.01)

(58) Field of Classification Search
CPC . A61F 2/01–013; A61F 2002/011–018; A61B 17/0057; A61B 17/12022–12045; A61B 17/12122; A61B 17/121131; A61B 17/1213–12154; A61B 17/12163–12177; A61B 2017/00575–00632; A61B 2017/00641; A61B 17/12109;
(Continued)

(56) References Cited

U.S. PATENT DOCUMENTS 6,080,182 A    6/2000  Shaw et al.
6,994,092 B2 *  2/2006  van der Burg ..... A61B 17/0057
                                              128/887
(Continued)

OTHER PUBLICATIONS

Office Action corresponding European Application No. 14 861 311.0.
(Continued)

*Primary Examiner* — Todd J Scherbel
(74) *Attorney, Agent, or Firm* — Maier & Maier, PLLC (57) ABSTRACT

The present invention relates to a left atrial appendage occluder having a sealing disc and a fixing bracket which is connected to the sealing disc and located at one side of the sealing disc; the fixing bracket comprising a connecting portion connected to the sealing disc, and a plurality of supports. After radiating out distally from the connecting portion, the plurality of supports are bent to extend proximally to form a plurality of spaced suspended supporting segments. The left atrial appendage occluder further includes a thin film, with all the supports being connected through the thin film.

20 Claims, 6 Drawing Sheets

(58) Field of Classification Search
CPC ...... A61B 17/1215; A61B 2017/12004; A61B 17/1214
See application file for complete search history.

(56) References Cited

U.S. PATENT DOCUMENTS

| | | | |
|---|---|---|---|
| 2003/0057156 A1* | 3/2003 | Peterson | A61B 17/12022 210/645 |
| 2003/0181942 A1 | 9/2003 | Sutton et al. | |
| 2005/0070952 A1* | 3/2005 | Devellian | A61B 17/0057 606/200 |
| 2006/0009800 A1* | 1/2006 | Christianson | A61B 17/0057 606/213 |
| 2008/0071298 A1 | 3/2008 | Khairkhahan et al. | |
| 2009/0099596 A1* | 4/2009 | McGuckin, Jr. | A61B 17/0057 606/216 |
| 2010/0324585 A1* | 12/2010 | Miles | A61B 17/0057 606/198 |
| 2010/0324595 A1* | 12/2010 | Linder | A61B 17/0057 606/213 |
| 2011/0054515 A1 | 3/2011 | Bridgeman et al. | |
| 2012/0172927 A1 | 7/2012 | Campbell et al. | |
| 2012/0172979 A1 | 7/2012 | DuMontelle | |
| 2012/0283585 A1* | 11/2012 | Werneth | A61B 17/0057 600/508 |
| 2013/0035714 A1* | 2/2013 | Snow | A61F 2/01 606/200 |
| 2013/0178889 A1 | 7/2013 | Miles et al. | |
| 2014/0005714 A1* | 1/2014 | Quick | A61L 31/022 606/200 |
| 2015/0342612 A1* | 12/2015 | Wu | A61B 17/12031 606/200 |

OTHER PUBLICATIONS

First Office Action for corresponding China Application No. 201310567987.0.
Written Opinion dated Oct. 30, 2017 for corresponding China Application No. 201480073126.X.
Search Report for corresponding China Application No. 201310567987.0.
Written Opinion for corresponding Korea Application No. 10-2016-7013720.
Notification of Reason for Refusal dated Sep. 5, 2017 for corresponding Korea Application No. 10-2016-7013720.

* cited by examiner

Figure 12

LEFT ATRIAL APPENDAGE OCCLUDER

TECHNICAL FIELD

The present invention relates to medical devices, in particular to an occluder which is capable of being transferred to a predetermined position in the human body by an interventional catheterization technique, and preventing stroke caused by thrombosis in the left atrial appendage due to atrial fibrillation.

BACKGROUND OF THE PRESENT INVENTION

At present, therapy for treating diseases by interventional catheterization technique is widely applied, and a variety of materials, apparatuses and drugs are placed into the heart, arteries and veins of the human body through this treatment.

When an occluder is placed into the heart, arteries, veins, and left atrial appendage by the catheter interventional method, due to complex anatomical structures of the heart, the artery and vein blood vessels, especially the left atrial appendage, the apparatus is required to be delivered to a predetermined position accurately, and to be well-adapted to the anatomical structure, mechanics requirements and hemodynamics requirements of the predetermined position at the same time. Under the premise of only generating microtrauma to the human body, firstly, the skin near the blood vessel is punctured, a guide wire enters into the blood vessel from the puncturing site, one end of a catheter is delivered to the predetermined position under the guidance of the guide wire, and the other end thereof is reserved in vitro, and then the apparatus is transferred to the predetermined position by using the catheter and a pusher. During such procedure, a fine flexible catheter is required, while the catheter and the guide wire are designed to be visualized under the X ray. Once the catheter reaches the predetermined position, the guide wire is removed, and the apparatus is guided to the tail end of the catheter by using an access established by the catheter through the pusher; when being completely exposed from the tail end of the catheter, the apparatus is released from the pusher.

For example, the occluder is placed into the left atrial appendage by using the catheter interventional method, in order to prevent thrombosis from the left atrial appendage causing atrial fibrillation, and stroke caused by ascending the thrombus to the brain; or in order to prevent systemic embolism caused by the thrombus reaching to other parts of the body through a body blood circulation system. Placing the occluder into the left atrial appendage to occlude the left atrial appendage and block the blood flow entering into the left atrial appendage can eliminate the risk of thrombosis formed in the left atrial appendage, thus preventing stroke. At present, the apparatuses are usually threadedly connected to a delivery sheath.

Figure 1:
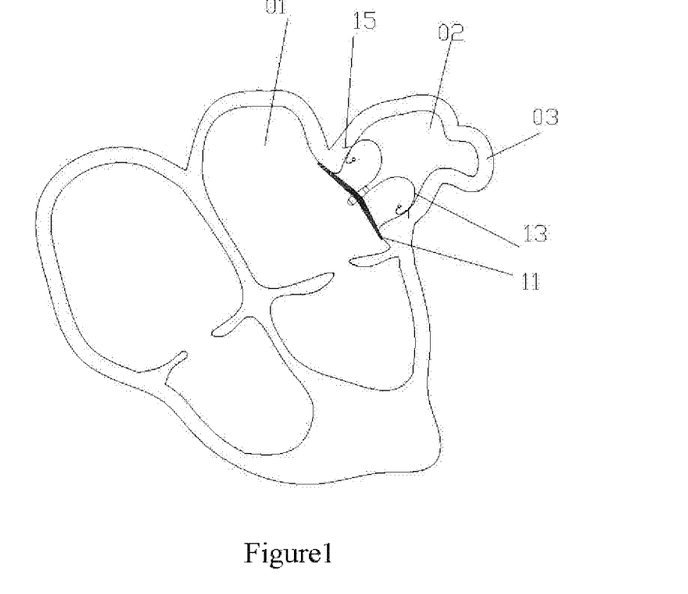
FIG. 1 is a diagram showing an existing left atrial appendage occluder in an anatomical structure of the heart and the left atrial appendage.
Figure 2:
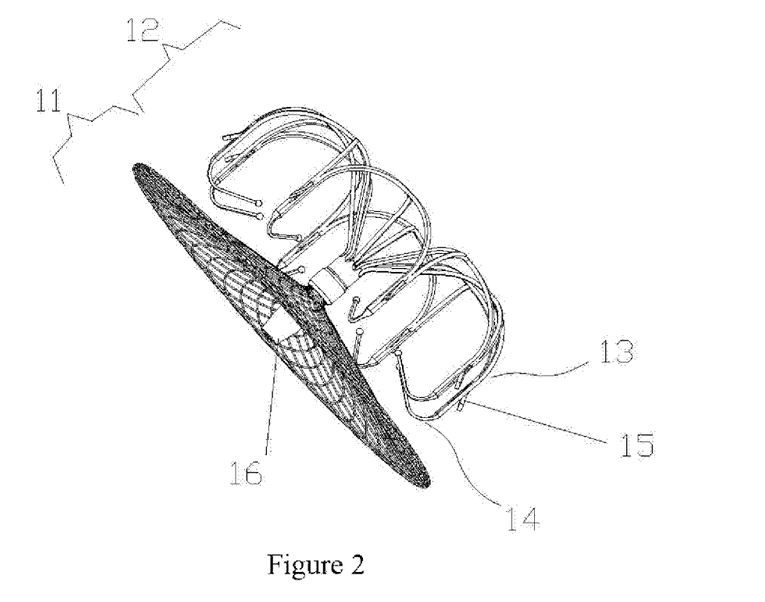
FIG. 2 is a structure diagram of the existing left atrial appendage occluder.

With reference to FIG. 1 and FIG. 2, FIG. 1 shows an existing left atrial appendage occluder located in an anatomical structure of the heart and the left atrial appendage, and FIG. 2 is a structure diagram of the existing left atrial appendage occluder, wherein 01 means left atrium, 02 means left atrial appendage and 03 means left atrial appendage cavity wall. The occluder includes a sealing disc 11 and a fixing bracket 12 which consists of a plurality of supports 13; a fixing anchor (or referred to as anchoring barb) 15 is arranged on each of the supports 13, and the supports 13 are extended to ball ends of support ends 14 starting from a position where the fixing anchor 15 is located, and spaced from each other; a connecting nut 16 is arranged on the sealing disc 11 of the left atrial appendage occluder. The occluder has good elasticity, may be contained in a sheath with width of 2 to 4 mm, transferred into the left atrial appendage 02 through the vascular access, and slowly retreated from the sheath tube; the fixing bracket 12 of the occluder will be unfolded in the left atrial appendage cavity, and the supports 13 of the fixing bracket 12 will be pressed on the left atrial wall by adapting to the shape of the left atrial appendage 02, while the fixing anchor 15 of the supports 13 will be penetrated into the inner wall 03 of the left atrial appendage, thus guaranteeing reliable fixation, and, the sealing disc 11 is covered on the ostium of the left atrial appendage 02, as shown in FIG. 1. Finally, a steel cable connected to the left atrial appendage occluder is released, thus occluding the left atrial appendage and blocking the blood flow entering into the left atrial appendage.

The above left atrial appendage occluder has the following limitations: the support ends of the fixing bracket are spaced and suspended. When the fixing bracket is pushed out after being placed into the sheath tube, the risk of twisting between the support ends exists, resulting in possible failure of the fixing bracket to unfold properly, and therefore a failed procedure.

SUMMARY OF THE PRESENT INVENTION

An object of the present invention is to provide a left atrial appendage occluder, that avoids twisting between the supports.

The present technical solution is to provide a left atrial appendage occluder, including a sealing disc and a fixing bracket which is connected to the sealing disc and located at one side of the sealing disc; the fixing bracket including a connecting portion connected to the sealing disc, and a plurality of supports; after radiating out distally from the connecting portion and coordinating to form a recessed area, the plurality of supports are bent to extend proximally to form a plurality of spaced suspended supporting segments, the supporting segment being provided with at least one anchoring barb facing the sealing disc; the left atrial appendage occluder further includes a thin film, all the supports being connected in series through the thin film.

In the left atrial appendage occluder according to an embodiment of the present invention, the thin film includes at least one annular thin film which is fixed on all the supports and encircles the recessed area to expose the whole or a part of the recessed area.

In the left atrial appendage occluder according to an embodiment of the present invention, the thin film includes a spherical thin film further covering the recessed area.

In the left atrial appendage occluder according to an embodiment of the present invention, at least one anchoring barb penetrates through the thin film.

In the left atrial appendage occluder according to an embodiment of the present invention, the thickness of a portion of the thin film located surrounding the anchoring barb is larger than or equal to that of the rest portion of the thin film.

In the left atrial appendage occluder according to an embodiment of the present invention, the supports are further provided with a plurality of fixing holes, through which the thin film is fixed on the supports by suturing.

In the left atrial appendage occluder according to an embodiment of the present invention, the thin film is adhered on the supports through biocompatible adhesive.

In the left atrial appendage occluder according to an embodiment of the present invention, a proximal edge of the thin film is 1 to 5 mm away from a root of the anchoring barb.

In the left atrial appendage occluder according to an embodiment of the present invention, after penetrating through the thin film, the length of the anchoring barb extending outside is between 1 mm and 3 mm.

In the left atrial appendage occluder according to an embodiment of the present invention, the thin film is made of PET or PTFE or silica gel.

In the left atrial appendage occluder according to an embodiment of the present invention, the thin film includes a plurality of overlapped thin film layers.

In the left atrial appendage occluder according to an embodiment of the present invention, the thin film includes multiple sheets of thin film distributed at interval on the fixing bracket along the direction from the distal end to the proximal end.

In the left atrial appendage occluder according to an embodiment of the present invention, the number of the supports is six, eight, nine, twelve, or sixteen.

In the left atrial appendage occluder according to an embodiment of the present invention, the anchoring barb is formed on the supports by cutting.

In the left atrial appendage occluder according to an embodiment of the present invention, the supports include a plurality of guiding segments, a plurality of branching segments and a plurality of suspended supporting segments successively radiating out distally from the connecting portion.

In the left atrial appendage occluder according to an embodiment of the present invention, the plurality of guiding segments are coordinated with each other to form a recessed area by regarding the connecting portion as a center; one end of each guiding segment away from the connecting portion is respectively connected to two branching segments; the two branching segments form an included angle; each branching segment is intersected with one of the two branching segments corresponding to the adjacent guiding segment which is adjacent thereto, and bent to extend proximally to form the suspended supporting segments.

In the left atrial appendage occluder according to an embodiment of the present invention, the suspended supporting segments are approximately U-shaped.

In the left atrial appendage occluder according to an embodiment of the present invention, the tail ends of the suspended supporting segments are provided with spheres.

In the left atrial appendage occluder according to an embodiment of the present invention, the supports are formed by cutting a nickel-titanium tube from one end thereof along the direction towards another end, expanded by using a mould, and shaped by heat treatment; the portion of the nickel-titanium tube which is not cut off forms the connecting portion.

Compared with the prior art, the technical solution employed by the present invention at least has the following advantages: the left atrial appendage occluder further includes the thin film through which all the supports are connected in series, the present invention effectively restrains the relative position and relative movement between the supporting segments through the thin film, thus avoiding twisting of the supporting segments when the fixing bracket is pushed out and released from a delivery sheath.

BRIEF DESCRIPTION OF THE DRAWINGS

The present invention will be further illustrated as below with reference to accompanying drawings and embodiments, in the drawings:

FIG. 4 is a schematic diagram of the left atrial appendage occluder as shown in FIG. 3 from another view;

DETAILED DESCRIPTION OF THE PRESENT INVENTION

In order to understand the object, the technical solution and the advantages of the present invention more clearly, the present invention will be further described in detail with reference to the accompanying drawings and embodiments. It should be understood that the specific embodiments described hereinafter are only used for explaining the present invention, but not for limiting the present invention.

In order to more clearly describe the structure of the left atrial appendage occluder (hereinafter referred to as occluder), terms such as 'distal end' and 'proximal end" are defined. The above terms are commonly used in the field of interventional medical device. Specifically, the term 'distal end' means the end away from an operator during surgery, and the term 'proximal end' means the end near the operator during surgery.

With reference to FIG. 3 to FIG. 8, an embodiment of the present invention provides a left atrial appendage occluder 10 that includes a sealing disc 100, a fixing bracket 200 connected to the sealing disc 100 and located at one side of the sealing disc 100, and a thin film 300 fixed on the fixing bracket 200.

Figure 3:
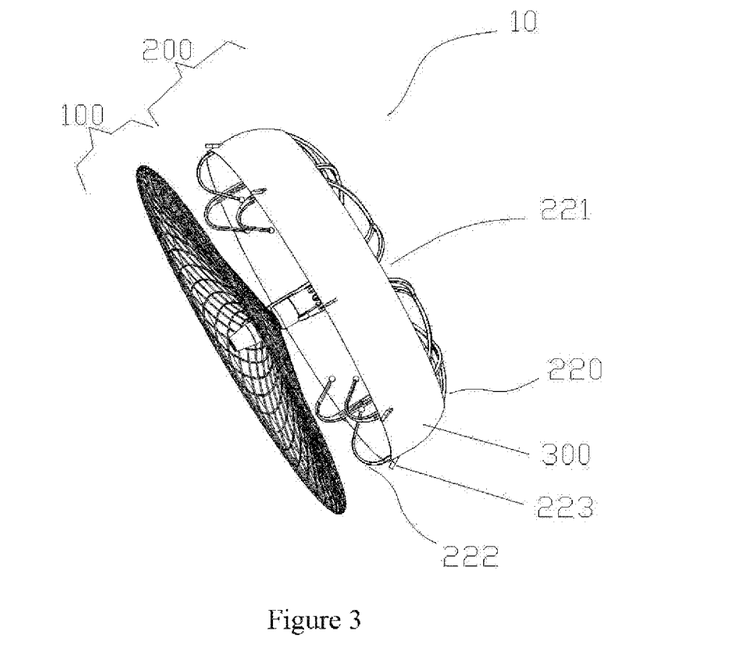
FIG. 3 is a schematic diagram of a left atrial appendage occluder provided by an embodiment of the present invention.

The sealing disc 100 is formed by braiding a nickel titanium wire or a biocompatible polymer wire, and located at the proximal end relative to the fixing bracket 200.

The fixing bracket 200 includes a connecting portion 210 connected to the sealing disc 100, and a plurality of supports 220. After radiating out distally from the connecting portion 210 and coordinating to form a recessed area 221, the plurality of supports 220 are bent to extend proximally to form a plurality of spaced suspended supporting segments 222, the supporting segments 222 are provided with at least one anchoring barb 223 facing the sealing disc 100.

In actual manufacturing, the plurality of supports 220 may be formed by cutting a nickel titanium tube from one end thereof along the direction towards the other end, expanded by using a mould, and shaped by heat treatment; the portion of the nickel-titanium tube which is not cut off forms the connecting portion 210. The number of the supports 220 may be determined according to the requirements of the mechanical properties and size specifications, such as six, eight, nine, twelve, and sixteen, etc. During the cutting, the anchoring barb 223 arranged on the supports 220 is cut off at the same time.

Figure 5:
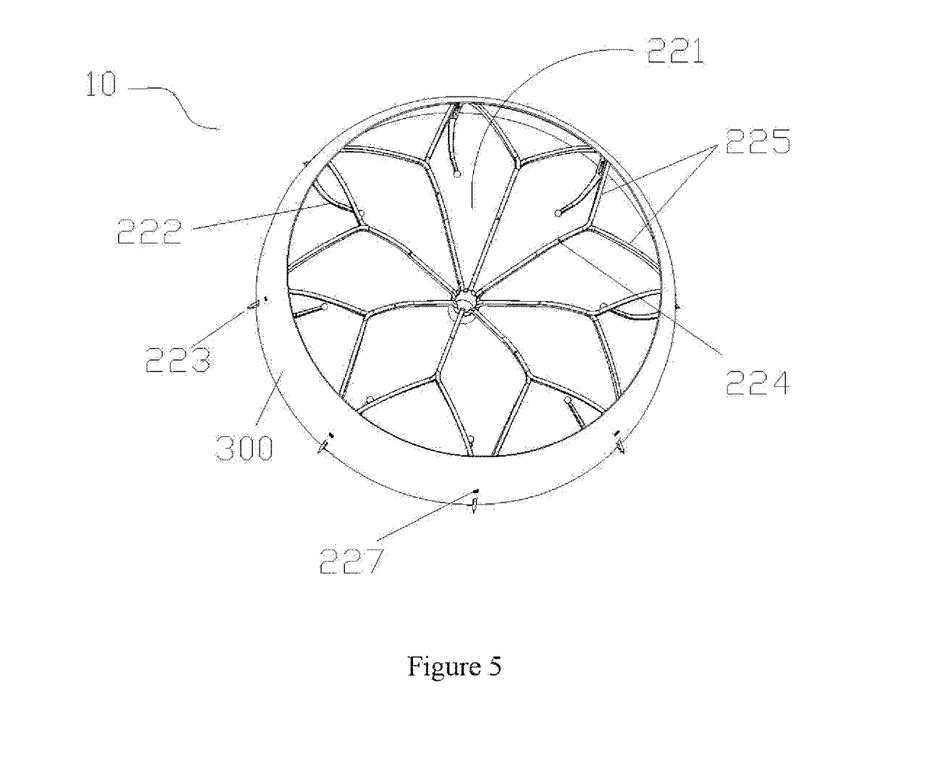
FIG. 5 and FIG. 6 show a schematic diagram of a fixing bracket in FIG. 3.
Figure 6:
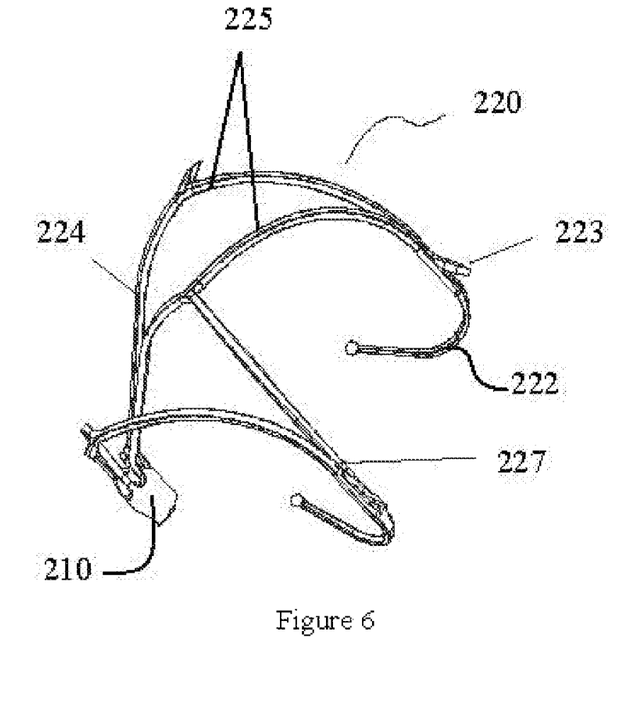

With reference to FIG. 5 to FIG. 6, the supports 220 include a plurality of guiding segments 224, a plurality of branching segments 225 and a plurality of suspended supporting segments 222 successively radiating out distally from the connecting portion 210. The plurality of guiding segments 224 are coordinated with each other to form a recessed area 221 by regarding the connecting portion 210 as a center. One end of each guiding segment 224 away from the connecting portion 210 is respectively connected to two branching segments 225. The two branching segments 225 form an included angle, preferably, an acute angle. Each branching segment 225 is intersected with one of the two branching segments corresponding to the adjacent guiding segment 224 which is adjacent thereto, and bent to extend proximally to form the suspended supporting segments 222. The supporting segments 222 are spaced from each other. In other words, each guiding segment 224, encircling the connecting portion 210, terminates into the two branching segments 225 connected thereto, to form a similar V-shaped or herringbone shape; and two adjacent V-shaped or herringbone structures, after being connected to one end away from the connecting portion 210, are extended to form a supporting segment 222. The supporting segment 222 is approximately U-shaped, one end thereof connected to the branching segments 225 is provided with an anchoring barb 223, and the suspended end thereof is processed to form a sphere 226. With reference to FIG. 6, the ends of the guiding segments 224 and the branching segments 225 near the supporting segment 222 are all provided with a plurality of fixing holes 227.

Still as shown in FIG. 3 and FIG. 4, the thin film 300 is usually made of PET or PTFE or silica gel material, and may also be made of other thin film with biocompatibility and physical performance meeting the requirements. The thin film 300 includes an annular thin film fixed on all the branching segments 225 of the fixing bracket 200 in a manner of coordination of the anchoring barb 223 and suturing, thus being connected in series to all the supports 220 to expose the whole or a part of the recessed area 221. After the occluder 10 is released in the left atrial appendage, the thin film 300 constitutes the outer surfaces of the supports 220 in contact with the inner wall of the left atrial appendage. The suturing means that the suture passes through the fixing holes 227 and then passes through the annular thin film 300, and then is knotted to fix the thin film 300.

Figure 7:
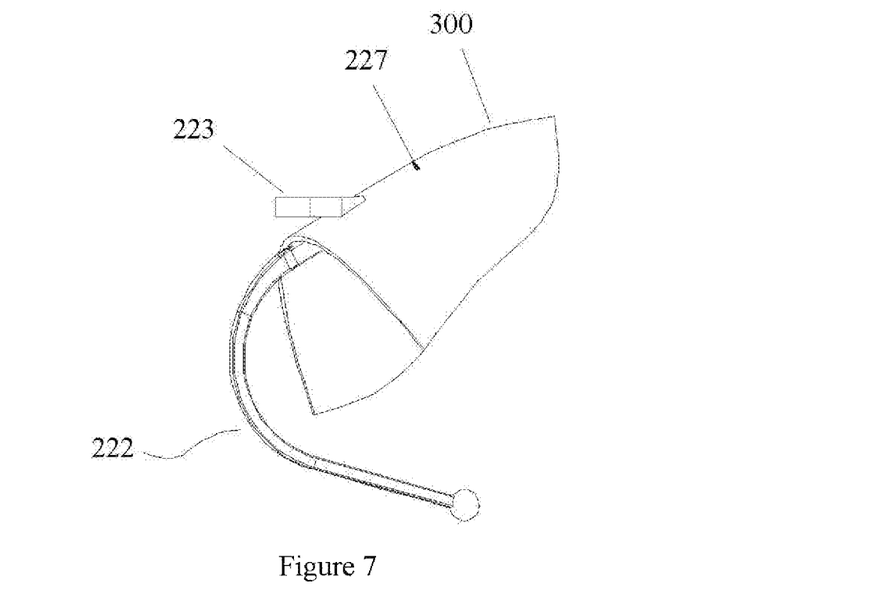
FIG. 7 shows a local diagram of a support and a thin film in FIG. 3.

As shown in FIG. 7, the width of the thin film 300 may be determined by a position from the anchoring barb 223 to the fixing holes 227 of the supports 220 of the fixing bracket 200 and the annular thin film 300. In the present embodiment, the thin film 300 may proximally extend 1 to 5 mm from the root of the anchoring barb 223, and the thin film 300 may distally extend 2 to 10 mm from the fixing holes 227 of the supports 220 and the annular thin film 300. The thickness of the thin film 300 shall meet the following conditions: after penetrating through the thin film 300, the length of the anchoring barb 223 extending out the thin film 300 is equal to or more than 1 mm and less than or equal to 3 mm, in order to ensure that the anchoring barb 223 will not fall off after being inserted into the left atrial appendage.

Figure 8:
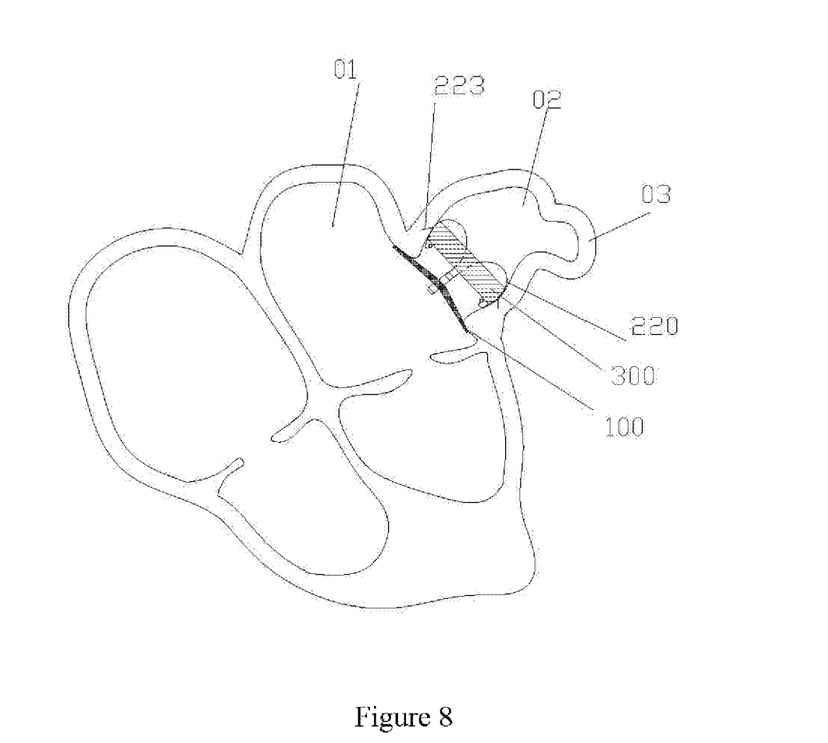
FIG. 8 shows a schematic diagram of the left atrial appendage occluder as shown in FIG. 3 after being released in the left atrial appendage.
Figure 9:
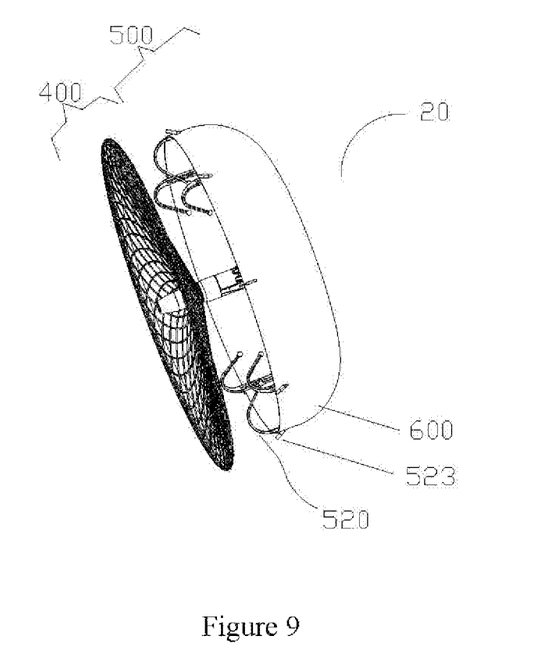
FIG. 9 is a schematic diagram of a left atrial appendage occluder provided by another embodiment of the present invention.
Figure 10:
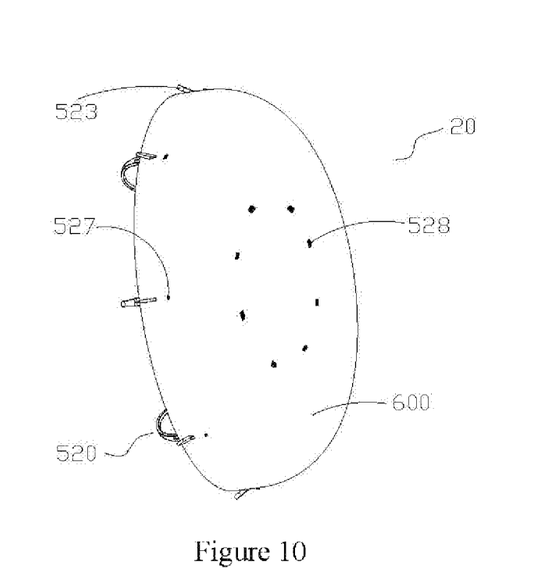
FIG. 10 is a schematic diagram of the left atrial appendage occluder as shown in FIG. 9 from another view.
Figure 11:
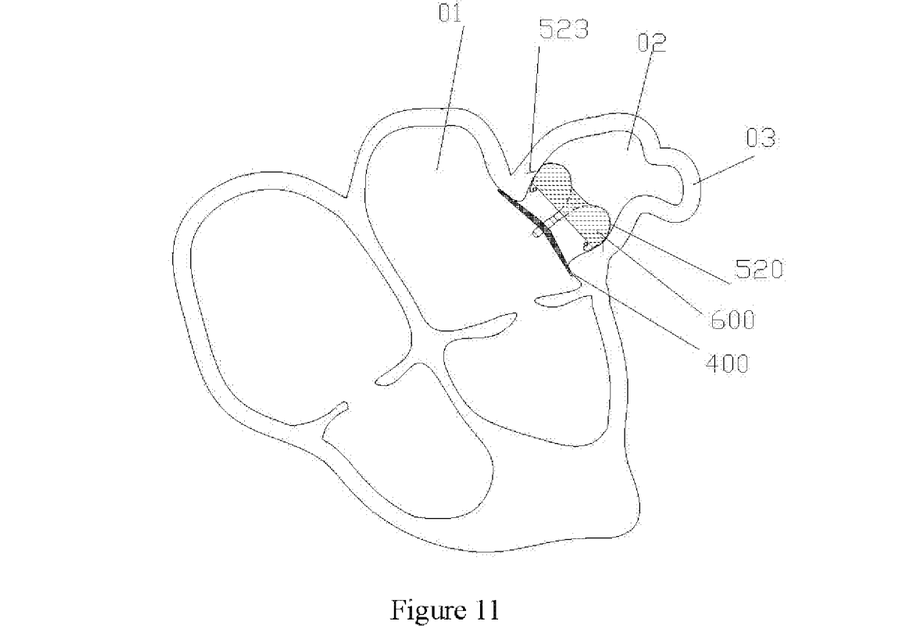
FIG. 11 is a schematic diagram of the left atrial appendage occluder as shown in FIG. 9 after being released in the left atrial appendage.

FIG. 8 shows a schematic diagram of the left atrial appendage occluder released in the left atrial appendage, as shown in FIG. 8, when the fixing bracket 200 is placed into the left atrial appendage, the fixing bracket 200 and the annular thin film 300 are unfolded in the state shown in FIG. 8, the supports 220 of the fixing bracket 200 and the annular thin film 300 are laminated together in the inner wall 03 of the left atrial appendage, the contact surface between the fixing bracket 200 and inner wall 03 is a cylindrical surface. This is compared with the existing left atrial appendage occluder as shown in FIG. 1 in which only each support 220 and the inner wall 03 are in contact, the contact area being enlarged dozens of times. In this way, the stress is more evenly distributed along the inner wall 03 so that the penetrating length of the anchoring barbs 223 on the supports 220 are approximately same into the inner wall 03. At the same time, the stress per unit area is smaller, thus avoiding damage to the inner wall 03 caused by excessive stress on a certain site.

Moreover, the thin film 300 plays a role of effectively restraining the relative position and relative movement between the supports 220. The thin film 300 has soft, thin, compressible and elastic characteristics, so that the thin film 300 can be always retained on the supports 220 and folded and unfolded along with the supports 220 in the process of placing the fixing bracket 200 into a delivery sheath and then pushing out from the delivery sheath, thus reducing or even avoiding the risk of twisting of the supports 220, and ensuring smooth operation of the procedure.

Further, due to the structure and size characteristics of the annular thin film 300, the edge thereof is at a certain distance from the root of the anchoring barb 223, when the anchoring barb 223 is penetrated into the inner wall 03 of the left atrial appendage to a certain depth, the annular thin film 300 will inhibit the anchoring barb 23 from moving deeply into the wall 03, such that the depth of the anchoring barb 223 penetrated into the wall 03 is controllable and extensive damage to the wall 03 caused by uneven stressing is decreased. In addition, in an extreme instance, such as the wall 03 is punctured by an anchoring barb 223, in accordance with the existing left atrial appendage occluder, blood will run out from the wall 03 and flow inside the left atrial appendage and then be seeped into the pericardial cavity from the pierced position, resulting in pericardial effusion, seriously resulting in cardiac arrest and threatening life. But for the present embodiment, once the wall 03 is punctured by the anchoring barb 223, the thin film 300 will immediately cover the punctured position while facilitating formation of microthrombus nearby, the throughhole resulted from the puncturing is blocked by the thrombus, such that the blood is prevented from seeping into the pericardial cavity, and the risk of pericardial effusion and even cardiac arrest is reduced. At the same time, the thin film can accelerate thrombosis of the blood in the left atrial appendage and then muscularize, and accelerate the process of muscularization of the left atrial appendage.

With reference to FIG. 9 to FIG. 12, a left atrial appendage occluder 20 provided by another embodiment of the present invention has a structure similar to that of the left atrial appendage occluder 10, including a sealing disc 400, a fixing bracket 500 connected to the sealing disc 400 and located at one side of the sealing disc 400, and a thin film 600 fixed on the fixing bracket 500. The difference of the occluder 20 from the left atrial appendage occluder 10 lies in that, the thin film 600 is spherical, a proximal edge thereof is 1 to 5 mm away from the root of an anchoring barb 523, and a distal part of the thin film 600 covers the whole recessed area (covered, not shown). The thin film 600 and the supports 520 are sutured together through the fixing holes 527, 528. Each group of the fixing holes 527 and 528 is arranged in the same positions on each support 520. The fixing manner is the same as that of the first embodiment.

Figure 12:
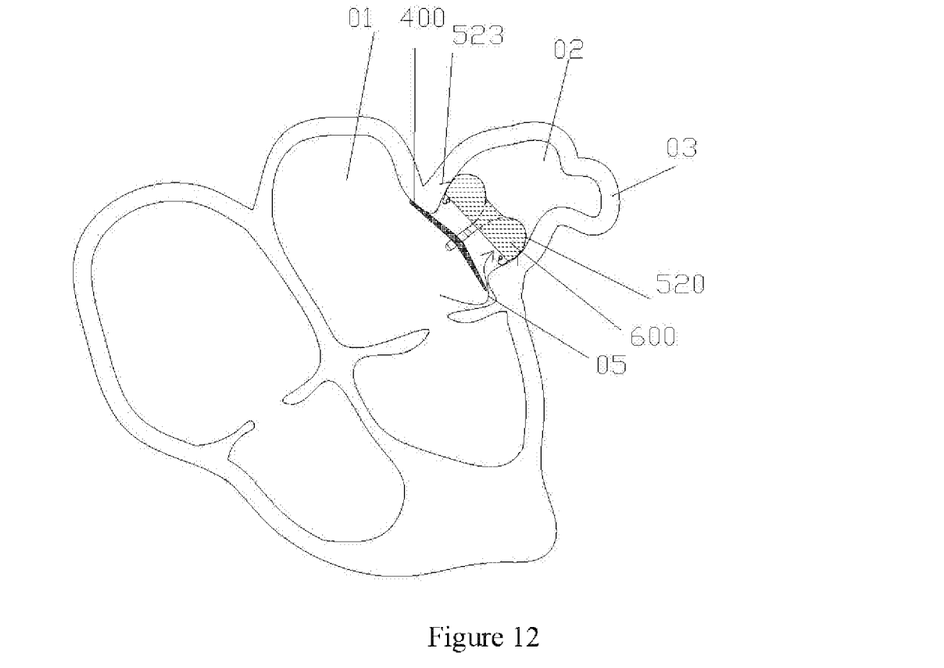
FIG. 12 is a schematic diagram of the left atrial appendage occluder as shown in FIG. 9 not completely occluding an entrance of the left atrial appendage in the process of releasing in the left atrial appendage.

In addition to the same action mechanism and advantages as the first embodiment, the thin film 600 further has the following characteristics as follows: in some extreme instances, such as shown in FIG. 12, the entrance of the left atrial appendage is not completely sealed by the sealing disc 11 of the left atrial appendage occluder, the blood may enter the left atrial appendage along the direction represented by an arrow 05, at this moment, the thin film 600 in the second embodiment will act as a second barrier near the entrance in the left atrial appendage, thus preventing the blood from entering into a deeper portion of the left atrial appendage and reducing the thrombosis risk.

Compared with the above embodiments, the left atrial appendage occluder of the present embodiment is capable of blocking the blood flow entering into a deeper position in the chamber of the left atrial appendage due to the entrance of the left atrial appendage not being completely sealed by the sealing disc 11 of the left atrial appendage occluder, thus reducing the thrombosis risk.

It is worth mentioning that, the thin film may have different thicknesses according to different areas in other embodiments of the present invention, for example, the thickness of a portion of the thin film located surrounding the anchoring barb is larger than or equal to that of the other portions of the thin film. Thus, once the wall of the left atrial appendage is punctured by the anchoring barb, the thickened thin film located surrounding the anchoring barb will more effectively prevent hemorrhage after the anchoring barb penetrates into the left atrial appendage, and accelerate thrombosis. In other embodiments, the thin film comprises laminated films, and more thin film layers are located surrounding the anchoring barb. For example, the thin film may include a first thin film layer which is an hemispherical thin film and a second thin film layer which is an annular thin film, the first thin film layer and the second thin film layer are laminated in the area surrounding the anchoring barb, to increase the thickness of the thin film in the area surrounding the anchoring barb. In other embodiments, the thin film includes multiple sheets of thin film distributed at interval on the fixing bracket along the direction from the distal end to the proximal end.

The thin film can be fixed in any suitable position of the supports, such as fixed at at least one of the recessed area, the guiding segments, the branching segments and the supporting segments, as long as the supports under a natural state are connected in series and fixed to the thin film. In addition, regardless of whether the anchoring barb is pierced through the thin film or not, the thin film may also be fixed on the supports in other ways except through suture. For example, the thin film can be adhered on the fixing bracket by biological glue. If the thin film is made of silica gel film, the liquid silica gel raw material can be adhered on the supports by heat treatment.

The above descriptions are just preferred embodiments of the present invention, but not for limiting the present invention. Any modification, equivalent replacement and improvement done within the spirit and principle of the present invention should be regarded as falling into the protection scope of the present invention.

The invention claimed is:

1. A left atrial appendage occluder having a distal end and a proximal end, comprising:
    a sealing disc provided at the proximal end of the occluder;
    a fixing bracket having a connecting portion at a first end and a plurality of supports at a second end, the plurality of supports extending out from the connecting portion in a distal direction towards the distal end of the occluder and being bent in a proximal direction towards the proximal end of the occluder, each support comprising a proximate end that extends out from the connecting portion, a free end, and a fixing hole with a corresponding anchoring barb, the anchoring barb extending from each support at a location between the fixing hole and the free end of each support; and
    a thin film arranged on the fixing bracket and secured in positions around a perimeter of at least a proximal end of the thin film via the fixing holes of each support, and
    wherein the fixing bracket is coupled to the sealing disc by the connecting portion and the fixing bracket is coupled to the thin film by the fixing holes of the plurality of supports and by the anchoring barbs of the plurality of supports penetrating through the thin film.

2. The left atrial appendage occluder according to claim 1, wherein each anchoring barb has a root, and the root of each anchoring barb is 1 to 5 mm away from the proximal end of the thin film.

3. The left atrial appendage occluder according to claim 1, wherein each of anchoring barb penetrates through the thin film by a length of between 1 mm and 3 mm.

4. The left atrial appendage occluder according to claim 1, wherein the thin film has a thickness, and the thickness of a portion of the thin film located surrounding each anchoring barb is larger than or equal to that of other portions of the thin film.

5. The left atrial appendage occluder according to claim 1, wherein the thin film comprises a plurality of laminated thin film layers.

6. The left atrial appendage occluder according to claim 1, wherein the corresponding anchoring barb from the support penetrates the thin film, and the fixing bracket is coupled to the thin film by the fixing holes and the corresponding anchoring barbs of the plurality of supports.

7. The left atrial appendage occluder according to claim 6, wherein the sealing disc has a first diameter and the fixing bracket has a second diameter, with the first diameter being greater than the second diameter.

8. The left atrial appendage occluder according to claim 7, wherein the plurality of supports are bent in the proximal direction towards the proximal end of the occluder to form plurality of spaced suspended supporting segments, each of the plurality of spaced suspended supporting segments comprises the anchoring barb and the free end of each support.

9. The left atrial appendage occluder according to claim 8, wherein each of the plurality of spaced suspended supporting segments is approximately U-shaped, and each of the plurality of spaced suspended supporting segments provides a sphere at the free end of each support.

10. The left atrial appendage occluder according to claim 8, wherein each of the supports comprises a guiding segment radiating outwardly from a connecting portion, two branching segments and one of the plurality of suspended supporting segments, wherein one end of the guiding segment away from the connecting portion is respectively connected to the two branching segments; each branching segment is intersected with one of the two branching segments corresponding to the guiding segment which is adjacent thereto, and then connected with one of the plurality of suspended supporting segments.

11. The left atrial appendage occluder according to claim 10, wherein the thin film is fixed on all the branching segments and covers at least a portion of each guiding segment.

12. The left atrial appendage occluder according to claim 11, wherein the thin film comprises a spherical thin film that covers all the guiding segments and the branching segments.

13. The left atrial appendage occluder according to claim 10, wherein the plurality of guiding segments define a recessed area by regarding the connecting portion as a center at the distal end of the occluder.

14. The left atrial appendage occluder according to claim 7, wherein the thin film is secured in the positions around the perimeter via the fixing hole of each support by suturing.

15. The left atrial appendage occluder according to claim 14, wherein the thin film extends around the perimeter toward the distal end of the occluder 2 to 10 mm from the positions at which the thin film is sutured to each fixing hole.

16. The left atrial appendage occluder according to claim 7, wherein the plurality of supports define a recessed area, when regarding the connecting portion as a center at the distal end of the occluder, from which the plurality of supports extend outwardly before being bent.

17. The left atrial appendage occluder according to claim 16, wherein the thin film comprises a spherical thin film that covers the recessed area.

18. The left atrial appendage occluder according to claim 7, wherein the thin film comprises multiple sheets of thin film distributed in intervals on the plurality of supports along the direction from the free end to the proximal end of each support.

19. The left atrial appendage occluder according to claim 6, wherein the thin film is devoid of a central opening at a distal end of the thin film.

20. The left atrial appendage occluder according to claim 1, wherein the thin film is devoid of a central opening at a distal end of the thin film.

\* \* \* \* \*